United States Patent [19]

Vandenbergh et al.

[11] Patent Number: 4,479,936

[45] Date of Patent: Oct. 30, 1984

[54] **METHOD FOR PROTECTING THE GROWTH OF PLANTS EMPLOYING MUTANT SIDEROPHORE PRODUCING STRAINS OF *PSEUDOMONAS PUTIDA***

[75] Inventors: Peter A. Vandenbergh; Carlos F. Gonzalez, both of Sarasota, Fla.

[73] Assignee: Microlife Technics, Inc., Sarasota, Fla.

[21] Appl. No.: 423,814

[22] Filed: Sep. 27, 1982

[51] Int. Cl.$^3$ ............... A01N 63/00; A61K 37/00; C12N 1/20; C12N 15/00; C12R 1/38; C12R 1/40; A01B 79/00; A01C 1/00

[52] U.S. Cl. ............... 424/93; 435/172.1; 435/253; 435/262; 435/267; 435/874; 435/877; 47/58

[58] Field of Search ............... 424/92, 93, 177; 435/253, 262, 267, 272, 874, 911, 877, 172, 948, 240, 241; 47/58

[56] References Cited

U.S. PATENT DOCUMENTS 4,352,886 10/1982 Phillis et al. ............... 435/262
4,452,894 6/1984 Olsen et al. ............... 435/253

OTHER PUBLICATIONS

Vandenbergh et al., *Chemical Abstracts* vol. 95, No. 200301 x, 1981 "Isolation and Genetic Characterization of Bacteria that Degrade Chloramatic Compounds".
Kloepper, Joseph W. et al., "Enhanced Plant Growth . . . " Nature, vol. 286, pp. 885–886 (1980).
Kloepper, Joseph W. et al., "*Pseudomonas Siderophores* . . . " Cur. Micro., vol. 4, pp. 317–320 (1980).
Kloepper, Joseph W. et al., "Relationship of in vitro . . . " Phytopathology, vol. 71, pp. 1020–1024 (1981).
Cox, C. D. et al., Isolation of an Iron-Binding Compound from *Pseudomonas aeruginosa*, J. Bact. 137:357–364 (1979).
Meyer, J. M. et al., The Fluorescent Pigment of *Pseudomonas aeruginosa*: Biosynthesis, Purification and Physiochemical Properties., J. Gen. Micro. 107:319–328 (1978).
Meyer, J. M. et al., The Siderochromes of Non-fluorescent Pseudomonads: Production of Nocardamine of *Pseudomonas stutzeri* J. Gen. Micro. 118:125–129 (1980).
Teintze, M. et al., Structure of Ferric Pseudobactin, a Siderophore from Plant Growth Promoting Pseudomonas, Biochem. 20:6446–6457 (1981).
Jones, J. P. et al., Susceptibility of Resistant Tomato Cultivars to Fusarium Wilt, Phytopath. 64:1507–1510 (1974).

*Primary Examiner*—Thomas G. Wiseman
*Assistant Examiner*—Robin Teskin
*Attorney, Agent, or Firm*—Ian C. McLeod

[57] ABSTRACT

Plants susceptible to pathogenic fungi are contacted with a mutant strain of *Pseudomonas putida*, particularly *Pseudomonas putida* NRRL-B-12537 which produces iron complexing siderophores thereby affording protection from the fungi. The Pseudomonas competes with the fungi for iron found in the soil thereby inhibiting the fungi growth. The method is particularly effective in controlling *Fusarium oxysporum* Sp *lycopersici* on tomato plants.

12 Claims, No Drawings

METHOD FOR PROTECTING THE GROWTH OF PLANTS EMPLOYING MUTANT SIDEROPHORE PRODUCING STRAINS OF *PSEUDOMONAS PUTIDA*

SUMMARY OF THE INVENTION (1) Field of the Invention

The present invention relates to a method for protecting the growth of plants using an improved siderophore producing strain of *pseudomonas putida* particularly *Pseudomonas putida* NRRL-B-12,537 or an iron binding siderophore produced by the strain. The siderophore of the improved strain is significantly more active in repressing the growth of fungi than strains of Pseudomonas used by the prior art.

(2) Prior Art

Iron-binding compounds, called siderophores, have been isolated and purified from many bacteria. Bacteria that produce siderophores include *Escherichia coli, Bacillus megaterium,* Actinomyces sp., Mycobacterium sp., and the plant pathogen *Agrobacterium tumefaciens*. Pseudomonas strains related to the present invention are particularly described in Cox, C.D. and R. Graham. Isolation of an Iron-Binding Compound from *Pseudomonas aeruginosa*. J. Bact. 137:357–364 1979; Meyer, J. M. and M. A. Abdallah, The Fluorescent Pigment of *Pseudomonas fluorescens*: Biosynthesis, Purification and Physiochemical Properties. J. Gen Micro. 107:319–328 (1978); and Meyer, J. M. and M. S. Abdallah, The Siderochromes of Non-fluorescent Pseudomonads: Production of Nocardamine of *Pseudomonas stutzeri*. J. Gen. Micro. 118:125–129 (1980).

A specific strain of the *Pseudomonas fluorescens—putida* group, designated B10, recently has been used as seed inoculant on crop plants to promote growth and increase yields as described in, Kloepper, J. W., Leong, J., Teintze, M. and M. N. Schroth, Enhanced plant growth by siderophores produced by plant growth promoting rhizobacteria. Nature. 286:885–886 (1980); Kloepper, J. W., Leong, J., Teintze, M. and M. N. Schroth, Pseudomonas Siderophores: A Mechanism Explaining Disease—Suppressive Soils. Cur. Micro. 4:317–320 (1980); and Kloepper, J. W. and M. N. Schroth, Relationship of in vitro Antibiosis of Plant Growth-Promoting Rhizobacteria to Plant Growth and the Displacement of Root Microflora. Phytopath. 71:1020–1024 (1981). Pseudobactin, an iron-binding siderophore isolated from the above B10 strain, has been found to be a linear hexapeptide as described by Teintze, M., Hossain, M.B., Barnes, C. L., Leong, J. and D. Van der Helm, Structure of Ferric Pseudobactin, a Siderophore from Plant Growth Promoting Pseudomonas. Biochem. 20:6446–6457 (1981). B10 has the ability to enhance growth of the potato through the prevention of growth of certain phytopathogenic microorganisms.

As can be seen from the prior art, pseudomonads produce a variety of siderophore compounds. *Pseudomonas aeruginosa* produces a compound called pyochelin, a phenolic-like molecule that has no hydroxymate group. *P. stutzeri* produces a colorless trihydroxamate termed; nocardamine, which form stable complexes with ferric iron. Each of the siderophores appears to be different based upon the particular strain.

OBJECTS

It is therefore an object of the present invention to provide novel strains of *Pseudomonas putida* which exhibit improved plant growth protection in the presence of phytotoxic microorganisms by comparison to Pseudomonas sp. B10 and other similar Pseudomonas sp. It is further an object to produce novel iron-binding siderophores produced by such strains. These and other objects will become increasingly apparent by reference to the following description.

GENERAL DESCRIPTION

The present invention relates to a method for protecting the growth of a higher plant in the presence of phytopathogenic microorganisms which inhibit the growth of the plants which comprises contacting the plant or the soil around the plant with a phytopathogenic microorganism growth inhibiting amount of (1) a strain of *Pseudomonas putida* producing a siderophore similar to that produced by NRRL-B-12537 or (2) the siderophore produced by the strain, wherein the *Pseudomonas putida* strain grows in the presence of at least 2.5 mg per ml of ethylenediamine-di-(o-hydroxyphenyl acetic acid) (EDDA) in a growth medium containing ferric iron complexed by the EDDA due to the re-complexing of the iron by the siderophore. The present invention also relates to the siderophore having a Rf value of about 0.5 particularly the siderophore produced by the strain *Pseudomonas putida* NRRL-B-12537 in substantially pure form or in combination with an agriculturally acceptable carrier for application on or around a higher plant. The dosage used is preferably at least about $1 \times 10^4$ cells per gram of soil.

The present invention relates to a soil pseudomonad which produces an iron chelating compound which is chromatographically different when compared to pseudobactin prepared from Pseudomonas sp. B10 and other siderophores of the prior art. The thin layer chromatograms of the siderophores are discussed hereinafter.

*Pseudomonas putida* NRRL-B-12537 was isolated from soil adjacent to an oil well containing crude oil and had adapted to this harsh environment. The strain was isolated using the procedures and characterized as described in application Ser. No. 310,090 filed Oct. 9, 1981, now allowed U.S. Pat. No. 4,452,894. This application describes compositions of selected strains of Pseudomonas bacteria having the ability to utilize halogenated aromatic compounds as a sole carbon source. The bacteria are isolated from environments where they have been in long association with halogenated aromatic compounds, usually analagous compounds. First L-tryptophan and then a halogenated aromatic hydrocarbon are used as sole carbon sources for isolating and testing the selected strains. The isolated Pseudomonas strain of concern to the present invention is *Pseudomonas putida* NRRL-B-12537; which is useful for degrading halogenated aromatic pollutants, particularly mono- and di-chloroaromatics. Thus this strain was not isolated from soils used for the growth of food or other commercial crops as was Pseudomonas sp B10 and the related strains of Kloepper et al. *Pseudomonas putida* NRRL-B-12537 has the ability to degrade m-chlorotoluene as described in Ser. No. 310,090; however, this property in itself does not seem to be directly related to the present invention. It is believed that the oil impregnated soil environment over long periods of time evolved *Pseudomonas putida* NRRL-B-12537 into a fierce competitor for available ferric iron which accounts for its ability to suppress phytopathogenic microoganisms. Other oil well isolates did not appear to produce siderophores.

As used herein the term "plant" includes seeds or any growing portion of a higher plant. The growth protection of plants results from the inhibition of growth of the phytopathogenic microorganisms by the siderophore from Pseudomonas putida NRRL-B-12537 set forth in detail hereinafter.

SPECIFIC DESCRIPTION

(1) Materials and Methods

Bacterial strains.
The bacterial strains are listed in Table 1.

TABLE 1

| Strains | Relevant phenotype |
|---|---|
| Pseudomonas sp. B10 NRRL-B-15126 | prototroph |
| Pseudomonas sp. FP NRRL-B-15125 | prototroph |
| Pseudomonas sp. I24 NRRL-B-15124 | prototroph |
| Pseudomonas putida PPU3. NRRL-B-12537 | prototroph |
| Pseudomonas putida PPU3.1 NRRL-B-15122 | Sm$^r$ (b) |
| Pseudomonas putida PPU3.3 NRRL-B-15123 | EDDA$^-$ (a) |
| Pseudomonas putida ATCC 12633 | prototroph |
| Pseudomonas aeruginosa PAO1c NRRL-B-15136 | prototroph |

(a) EDDA, ethylenediamine-di-(o-hydroxyphenylacetic acid) The minus indicates a strain which can not capture ferric iron from EDDA.
(b) Sm$^r$, streptomycin resistance (1,000 µg per ml) Bacterial cultures were maintained on Pseudomonas Agar F (Difco Laboratories, Detroit, Michigan).

Fungal strains.
The strains used are readily available to those skilled in the art. Isolates used in the fungal inhibition assay were obtained from Dr. James DeVay, University of California, Department of Plant Pathology, Davis, Calif. Fusarium oxysporum f. sp. lycopersici race 1 utilized in the plant growth studies was obtained from Dr. John P. Jones, Agricultural Research and Education Center, Bradenton, Fla. Fungal cultures were maintained on Potato Dextrose Agar (Difco).

Isolation of mutants.
The mutagenesis procedure used was based on the method of R. H. Olsen, University of Michigan, Ann Arbor, Mich. Approximately $2 \times 10^9$ CFU in the exponential growth phase were concentrated and incubated with 400 µg of 1-methyl-3-nitro-1-nitrosoguanidine (NTG) (Sigma Chemical Co., St. Louis, MO) per ml at 25° C. for 30 minutes. The NTG exposed cells were centrifuged at 12,000×g for 15 minutes at 25° C. The pellets were then resuspended in a glucose-minimal broth (VBG) supplemented with 0.02% casamino acids, vitamin free (Difco) 0.05 mM tryptophan (Sigma), 0.05 mM adenine (Sigma) and 0.05 mM uracil (Sigma), then incubated for 2 hours at 25° C. as described in Vogel, H. J. and D. M. Bonner. Acetylornithinase of E. coli partial purification and some properties. J. Biol. Chem. 281:97-106 (1956). The siderophore deficient (negative) mutants were characterized by plating the NTG exposed cells onto VBG supplemented with 1.25 mg/ml ethylenediamine-di-(o-hydroxyphenylacetic acid) (EDDA) (Sigma).

Purification of the siderophore compound.
Pseudomonas sp. B10, P. putida PPU3. and P. putida 12633 were grown in 1 liter volumes in a glucose-minimal salts medium (VBG) incubated at 25° C. for 24 hours with vigorous shaking as described in Vogel, H. J. and D. M. Bonner. Acetylornithinase of E. coli partial purification and some properties. J. Biol. Chem. 281:97-106 (1956). The bacteria were removed by centrifugation, (9000×g for 15 minutes at 25° C.), and the supernatant was collected, concentrated and purified as described by Meyer et al (1978).

The resulting residue was dissolved in methanol and checked for purity using thin-layer chromatography with a solvent of water, acetic acid, acetone in a ratio of (90:5:1) by volume. A 15 microliter spot was used with saturation of a chromatography jar and a silica gel G chromatographic plate. After development and drying the plates were viewed under ultraviolet light and the bands were determined. Rf values were determined by dividing the vertical distance the fluorescent spot migrated by the distance migrated by the solvent front.

Fungal inhibition assay.
All P. putida and Pseudomonas sp. isolates were propagated at 25° C. on 10 ml of Pseudomonas Agar F (Difco). These plates were atomized with spore suspensions of each of the fungal cultures. The plates were incubated at 25° C. and read after 48 hours.

Plate growth studies.
Experiments on the growth promotion of P. putida and Pseudomonas sp. strains by the siderophore compound were constructed utilizing the methodology of Cox et al. All bacterial isolates were grown on VBG medium and then tested for growth on VBG supplemented with EDDA. This iron chelator compound, was incorporated into the VBG agar at final concentrations of 0.625, 1.25, 2.5 and 5.0 mg/ml.

Plant Growth Studies.
Tomato plants (Lycopersicon esculentum Mill., 'Bonny Best' which is a wilt susceptible variety) were grown in a growth chamber with a 16 hour light cycle (530 foot candle), temperature at 30° C. during the daylight cycle and 21° C. during the dark cycle and with a relative humidity of 62%. The ten day old seedlings were grown and treated in the following manner according to the method described in Jones J. P. and P. Crill. Susceptibility of Resistant tomato cultivars to Fusarium wilt. Phytopath. 64:1507-1510 (1974). (A.) 25 seedlings were grown in sterile soil, root dipped into sterile water and transplanted into sterile soil. (B.) 25 seedlings were grown in sterile soil, root dipped in sterile water containing Fusarium oxysporum at a concentration of $10^3$ spores/ml and transplanted into sterile soil. (C.) 25 seedlings were grown in sterile soil, root dipped in sterile water containing Fusarium oxysporum at a concentration of $10^5$ spores/ml and transplanted into sterile soil. (D.) 25 seedlings were grown in sterile soil supplemented with Pseudomonas putida PPU3.1 (which was previously selected from PPU3. for streptomycin resistance so as to be identifiable) at a concentration of $10^7$ CFU/g soil, root dipped into sterile water containing Fusarium oxysporum at a concentration of $10^3$ spores/ml and transplanted into sterile soil. (E.) 25 seedlings were grown in sterile soil supplemented with Pseudomonas putida PPU3.1 at a concentration of $10^7$ CFU/g soil, root dipped into sterile water containing Fusarium oxysporum at a concentration of $10^5$ spores/ml and transplanted into sterile soil. (F.) 25 seedlings were grown in sterile soil supplemented with Pseudomonas putida PPU3.1 at a concentration of $10^7$ CFU/g soil, root dipped into a solution of sterile water and transplanted into sterile soil.

Root colonization assay

The ability of P. putida PPU3.1 to colonize plant roots in the growth chamber studies was demonstrated by planting the tomato seeds (cultivar 'Bonny Best') in sterile soil containing $10^7$ CFU/g soil. After 10 days the seedlings were removed from the soil and the roots were washed thoroughly in sterile water. The roots were then weighed and macerated. Dilutions of this slurry were plated onto Pseudomonas Agar F (Difco) containing streptomycin sulfate (Sigma) at a concentration of 1000 μg/ml.

Results

Initial growth experiments in low iron media were conducted using several different Pseudomonas isolates. The strains were examined for growth in such media containing the iron chelator EDDA.

Of the P. putida strains examined each isolate grew at one EDDA concentration of 1.25 mg/ml whereas at the 2.5 mg/ml level only P. putida PPU3. and P. putida ATCC12633 (The type strain in Bergey's 8th Edition (1974)) were able to form colonies. The results are shown in Table 2.

TABLE 2

Comparison of various Pseudomonas isolates for their ability to overcome the inhibitory effects of the iron chelator (EDDA)[a].

| Bacterial strain | Media VBG[b] + | | | | |
|---|---|---|---|---|---|
| | 0 | EDDA in 0.62 | mg/ml 1.25 | 2.5 | 5.0 |
| Pseudomonas putida ATCC 12633 | + | + | + | + | − |
| Pseudomonas putida PPU3.(NRRL-B-12537) | + | + | + | + | − |
| Pseudomonas putida PPU3.1 NRRL-B-15122 | + | + | + | + | − |
| Pseudomonas putida PPU3.3 NRRL-B-15123 | + | − | − | − | − |
| Pseudomonas sp B10 (NRRL-B-15126) | + | − | − | − | − |
| Pseudomonas sp. FP (NRRL-B-15125) | + | ± | ± | − | − |
| Pseudomonas sp. I24 (NRRL-B-15124) | + | − | − | − | − |
| Pseudomonas aeruginosa PAO1c (NRRL-B-15136) | + | + | + | + | + |

[a]EDDA = ethylenediamine-di-(o-hydroxyphenylacetic acid) (mg/ml).
[b]VBG = glucose minimal salts medium.
+ = growth
− = no growth
± = slight growth
Plates were incubated at 25° C. for 48 hours.

The mutant P. putida PPU3.3 was obtained through treatment of P. putida PPU3. with 1-methyl-3-nitro-1-nitrosoguanidine. Through mutagenesis siderophore production and transport deficient strains were obtained. P. putida PPU3.3, a production deficient mutant, was non-fluorescent and unable to grow in the presence of EDDA at any concentration. The P. aeruginosa PAO1c was the only strain able to form colonies at an EDDA concentration of 5 mg/ml; however, PAO1c is a pathogen and can not be used for plants. The remaining strains, Pseudomonas sp. B10, FP and 124 grew poorly or were unable to grow in the presence of EDDA.

Growth studies in the presence of EDDA indicated that the compounds elaborated by these bacteria might have inhibitory effect on soil fungi. Since the isolate P. putida PPU3. grew at a 2.5 mg/ml EDDA concentration, it was compared for its fungal inhibitory activity to Pseudomonas sp. B10, since this was considered to be the best of the prior art strains according to the publications. Fungal growth inhibition was observed on plates incubated with Pseudomonas sp. B10 and P. putida PPU3. respectively. The results are shown in Table 3.

TABLE 3

Comparison of fungal growth inhibition associated with P. putida PPU3., P. putida PPU3.3 and Pseudomonas sp. B10 and Pseudomonas putida ATCC 12633 strains.

| Fungal Species | Bacterial strain | | | |
|---|---|---|---|---|
| | ATCC12633 | PPU3. | PPU3.3 | B10 |
| Ustilago maydis | ND | + | − | − |
| Verticillium dahliae | ND | + | − | + |
| Fusarium oxysporum | + | ++ | − | + |
| Thielaviopsis basicola | ND | + | − | + |
| Aspergillus niger | + | + | − | − |
| Penicillium expansum | ND | ++ | − | + |
| Rhizopus stolonifer | ND | + | − | + |
| Geotrichum candidum | + | ++ | − | + |

− = no inhibitory zone produced.
+ = inhibitory zone produced, <10 mm in diameter.
++ = strong inhibitory zone produced, >10 mm in diameter.
ND = Not determined.
Inhibitory zone determination utilized isolated colonies.
Plates were incubated at 25° C. for 48 hours.

The Pseudomonas sp. B10 isolate did not inhibit the growth of Aspergillus niger, whereas the P. putida PPU3. strain exhibited strong inhibition against Fusarium oxysporum, Ustilago maydis, Penicillium expansum and Geotrichum candidum. The mutant isolate P. putida PPU3.3 did not inhibit the growth of any of the fungal isolates examined. Pseudomonas putida ATCC 12633 the type strain was not as effective as PPU3. for fungal inhibition.

Cultural supernatant extract preparations of Pseudomonas sp B10, P. putida PPU3. and Pseudomonas putida 12633 were purified and compared utilizing thin-layer chromatography. The $R_f$ values of these iron chelating compounds were 0.6, 0.5 and 0.3 respectively, using water, acetic acid and acetone as the solvent. This indicated that the siderophores were different.

Plants grown in the presence of absence of P. putida PPU3.1 were root dipped in a spore suspension of Fusarium oxysporum f. sp. lycopersici and grown under conditions favorable to the development of disease. The results depicted in Table 4 represent an average of two experimental trails.

TABLE 4

Percentage of wilt in Fusarium sensitive tomatoes grown in the presence or absence of PPU3.1.

| | Treatment[a] | Wilt Reaction Day 10 (%)[b] |
|---|---|---|
| (A) | control, no Fusarium, no culture | 0 |

TABLE 4-continued

Percentage of wilt in Fusarium sensitive tomatoes grown in the presence or absence of PPU3.1.

| Treatment[a] | | Wilt Reaction Day 10 (%)[b] |
|---|---|---|
| (B) | $10^3$ Fusarium | 56 |
| (C) | $10^5$ Fusarium | 91 |
| (D) | $10^3$ Fusarium + $10^7$ PPU3.1 | 8 |
| (E) | $10^5$ Fusarium + $10^7$ PPU3.1 | 41 |
| (F) | $10^7$ PPU3.1 | 0 |

[a]See materials and Methods for description
[b]Average of two trials

Tomato plants utilized in treatments B and C were grown in the absence of *P. putida* PPU3.1 (PPU 3. was selected for streptomycin resistance for identification purposes) and inoculated with a spore concentration of $10^3$ and $10^5$ spores/ml respectively. After 10 days these plants exhibited typical stunting, chlorosis and wilt symptons at a percentage of 56 and 91 respectively. Growth of the susceptible cultivar in the presence of *P. putida* PPU3.1 followed by exposure to the Fusarium culture at concentrations similar to treatments B and C, demonstrated that growth in the presence of the bacterium significantly reduced the percentage of diseased plants in each treatment. Plating of washed roots from plants grown in the presence of *P. putida* PPU3.1 demonstrated that the strain was able to colonize roots. *P. putida* 3.1 did not demonstrate any evidence of causing any disease in control plants.

Table 2 shows that pseudomonads differ in their ability to overcome the inhibitory effects of the iron chelator EDDA. The *P. putida* PPU3. and *P. putida* ATCC 12633 isolates grew whereas most of the Pseudomonas sp. were unable to form colonies in the presence of EDDA. The siderophore molecules differ in their ability to bind iron, (EDDA binding coefficient, $10^{33.9}$). The Pseudomonas sp. B10 strain has been reported to produce a siderophore molecule designated pseudobactin by Kloepper et al (1980). This molecule has a lower iron binding ability, than the compound produced by *P. putida* PPU3., based on comparative growth in the presence of increasing concentrations of EDDA.

The prior art plant studies have shown that selected strains of Pseudomonas sp. can significantly increase crop yields. This result was correlated with in vitro antibiosis studies utilizing representative soil bacterial and fungal isolates. The comparison in Table 3 of *P. putida* PPU3. with Pseudomonas sp. B10 demonstrates that both isolates had the ability to inhibit a variety of phytopathogenic fungi. The *P. putida* PPU3.3 strain which was unable to grow in the presence of EDDA, did not inhibit any of the fungal strains. This shows that the iron chelation effect of the siderophore produced by *P. putida* PPU3. was responsible for fungal inhibition.

Growth of the tomato seedling in the presence of the *P. putida* PPU3.1 strain demonstrated its ability to colonize the rhizosphere of the plants and to afford the growing plants a margin of protection when challenged with *Fusarium oxysporum* f. sp. *lycopersici*. The interaction of the bacterial isolate with the plants and its affinity for roots is analogous to other Pseudomonas sp. which have been shown to have rhizosphere competence. Kloepper et al, have demonstrated that the inhibition of root colonizing fungi with a siderophore producing pseudomonad has increased crop yield.

Examination of purified cultural extract preparations of *P. putida* PPU3. and Pseudomonas sp. B10 which utilized thin-layer chromatography, demonstrated that when these compounds were purified under similar conditions they were different.

*Pseudomononas putida* NRRL-B-12537 and related strains that are efficient plant root colonizers and also possess strong fungal inhibitory abilities through biochelation, can be used in the biological control of certain plant diseases.

Obvious mutant and genetically modified variants of *Pseudomonas putida* NRRL-B-12537 which have the siderophore producing capability can be used. The siderophore alone can be used preferably with a conventional agricultural carrier in a plant protecting amount. Also the results with tomatoes are directly translatable to other plants, including fruits, vegetables and flowers, which have a disease induced by microorganisms which require iron for growth.

We claim:

1. A method for protecting the growth of a higher plant against phytopathogenic fungi which inhibit the growth of the plant, and are found in the soil, which comprises contacting a fungicidally effective amount of *Pseudumonas putida* which has the identifying characteristics of *Pseudomonas putida* NRRL-B-12537 on the plant or in the soil around the plant.

2. The method of claim 1 wherein the strain is isolated from soil adjacent an oil well impregnated with crude oil from the well.

3. The method of claim 1 wherein the siderophore produced by the strain of *Pseudomonas putida* when dissolved in methanol and analyzed using thin layer chromatography has a Rf value of about 0.5 in water, acetic acid and acetone in a ratio of 90:5:1 by volume and developed on a silica gel chromatographic plate.

4. The method of claim 1 wherein said strain is able to grow in the presence of at least 2.5 mg per ml of ethylenediamine:-di-(o-hydroxyphenylacetic acid (EDDA) in a glucose minimal growth medium (VGB) which allows the strain to grow containing ferric iron complexed by the EDDA due to re-complexing of the iron by the siderophore.

5. The method of claim 1 wherein the strain is *Pseudomonas putida* NRRL-B-12537.

6. The method of claim 1 wherein the soil around the plant is contacted with a fungicidally effective amount of said strain of *Pseudomonas putida* which enables colonies to develop on the root of said plant.

7. The method of claim 1 wherein the contacting is effected by dipping the roots of the plant are dipped into a solution containing a fungicidally effective amount of said strain of *Pseudomonas putida* prior to planting of said plant in the soil.

8. The method of claim 7 wherein the solution is an aqueous solution.

9. The method of claim 7 wherein the fungicidally effective amount of said strain is determined by comparison of colony forming ability of said strain with a streptomycin resistant mutant strain of *Pseudomonas putida*.

10. The method of claim 9 wherein the streptomycin resistant mutant strain is *Pseudomonas putida* NRRL-B-15,122.

11. The method of claim 1 wherein the fungus is of the genus fusarium and the plant is a tomato plant.

12. The method of claim 11 wherein the Fusarium is *Fusarium oxysporum* sp*lycopersici*.

* * * * *

UNITED STATES PATENT AND TRADEMARK OFFICE
CERTIFICATE OF CORRECTION

PATENT NO. : 4,479,936

DATED : October 30, 1984

INVENTOR(S) : Peter A. Vandenbergh et al.

It is certified that error appears in the above-identified patent and that said Letters Patent is hereby corrected as shown below:

Column 6, line 57 "of" first occurrence should be -- or --.

Column 6, line 62 "trails" should be -- trials --.

Column 8, line 67 "splycopersici" should be -- sp. lycopersici --.

Signed and Sealed this

Twenty-eighth Day of May 1985

[SEAL]

Attest:

DONALD J. QUIGG

Attesting Officer

Acting Commissioner of Patents and Trademarks